(12) United States Patent
Steinhardt et al.

(10) Patent No.: US 8,888,846 B2
(45) Date of Patent: Nov. 18, 2014

(54) PASSIVE OSSICLE PROSTHESIS COMPRISING APPLICATOR

(75) Inventors: Uwe Steinhardt, Hirrlingen (DE); Heinz Kurz, Dusslingen (DE); Daniel Felix Awengen, Binningen (CH)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 884 days.

(21) Appl. No.: 12/690,351

(22) Filed: Jan. 20, 2010

(65) Prior Publication Data

US 2010/0191331 A1 Jul. 29, 2010

(30) Foreign Application Priority Data

Jan. 24, 2009 (DE) .......................... 10 2009 006 047

(51) Int. Cl.
*A61F 2/18* (2006.01)
*A61F 2/00* (2006.01)

(52) U.S. Cl.
CPC ............. *A61F 2/18* (2013.01); *A61F 2002/183* (2013.01); *A61F 2/0095* (2013.01)
USPC ........................................................ 623/10

(58) Field of Classification Search
CPC .... A61F 2/18; A61F 2/0095; A61F 2002/183
USPC ..................... 623/10; 606/106, 109
See application file for complete search history.

(56) References Cited

U.S. PATENT DOCUMENTS

| | | | |
|---|---|---|---|
| 5,171,240 A * | 12/1992 | Hanwong | 606/1 |
| 6,432,139 B1 * | 8/2002 | Elies et al. | 623/10 |
| 6,554,861 B2 | 4/2003 | Knox et al. | |
| 6,579,317 B2 | 6/2003 | Kurz | |
| 6,892,466 B2 * | 5/2005 | Kurz et al. | 33/512 |
| 7,603,788 B2 * | 10/2009 | Kurz et al. | 33/512 |

(Continued)

FOREIGN PATENT DOCUMENTS

| | | | | |
|---|---|---|---|---|
| DE | 20 2007 012 217 | | 1/2008 | |
| DE | 10 2008 015 117 B3 * | | 6/2009 | A61F 2/18 |

(Continued)

*Primary Examiner* — Andrew Iwamaye
(74) *Attorney, Agent, or Firm* — Michael J. Striker (57) ABSTRACT

An ossicle prosthesis has, at on one end, a first fastening element for connection to the tympanic membrane or a component of the ossicular chain, on the other end, a second fastening element for connection to a further component of the ossicular chain, or directly to the inner ear, and a connecting element that connects the two fastening elements in a sound-conducting manner, and it also includes an elongated applicator for transferring the ossicle prosthesis from a sterile packaging to the surgical site and for insertion into the middle ear or the auditory meatus, with a free end extending away from the prosthesis and used for handling purposes, and with an engagement part which is initially fastened to the prosthesis in a non-positive or form-fit manner, or via a material bridge which may be broken off or sheared off, and which may be detached and removed together with the applicator once the prosthesis has been inserted into the ear. This prosthesis may be removed from the sterile packaging and immediately inserted directly into the auditory meatus of the patient, or inserted into the middle ear in a standardized manner, without the use of additional tools, while ensuring that handling during surgery is optimal and tailored to the geometry of the prosthesis and ruling out the possibility of damage occurring via the gripping and transfer of the prosthesis.

4 Claims, 9 Drawing Sheets

(56) References Cited

U.S. PATENT DOCUMENTS

| | | | |
|---|---|---|---|
| 8,100,966 B2 * | 1/2012 | Steinhardt et al. | 623/10 |
| 8,128,694 B2 * | 3/2012 | Steinhardt et al. | 623/10 |
| 8,128,695 B2 * | 3/2012 | Steinhardt et al. | 623/10 |
| 2002/0045939 A1 * | 4/2002 | Kurz | 623/10 |
| 2004/0167624 A1 * | 8/2004 | Kurz et al. | 623/10 |
| 2007/0150057 A1 * | 6/2007 | Kurz et al. | 623/10 |
| 2008/0058831 A1 * | 3/2008 | Fujiwara | 606/109 |
| 2008/0058832 A1 * | 3/2008 | Fujiwara | 606/109 |
| 2009/0149697 A1 | 6/2009 | Steinhardt et al. | |
| 2009/0240330 A1 * | 9/2009 | Steinhardt et al. | 623/10 |
| 2009/0240331 A1 * | 9/2009 | Steinhardt et al. | 623/10 |
| 2009/0240332 A1 * | 9/2009 | Steinhardt et al. | 623/10 |
| 2010/0174292 A1 * | 7/2010 | Labadie et al. | 606/108 |

FOREIGN PATENT DOCUMENTS

| | | | |
|---|---|---|---|
| EP | 1 181 907 | 2/2002 | |
| EP | 2103281 A1 * | 9/2009 | A61F 2/18 |
| EP | 2103282 A1 * | 9/2009 | A61F 2/18 |
| WO | 02/069850 | 9/2002 | |

* cited by examiner

PASSIVE OSSICLE PROSTHESIS COMPRISING APPLICATOR

CROSS-REFERENCE TO A RELATED APPLICATION

The invention described and claimed hereinbelow is also described in German Patent Application DE 10 2009 006 047.2 filed on Jan. 24, 2009. This German Patent Application, whose subject matter is incorporated here by reference, provides the basis for a claim of priority of invention under 35 U.S.C. 119(a)-(d).

BACKGROUND OF THE INVENTION

The present invention relates generally to a passive ossicle prosthesis comprising an applicator. More particularly, the present invention relates to an ossicle prosthesis that replaces or bridges at least one component of the human ossicular chain, in the case of which the ossicle prosthesis includes, at one end, a first fastening element for mechanical connection to the tympanic membrane or a component of the ossicular chain, in particular to the limb of incus or the manubrium of malleus, and, at the other end, includes a second fastening element for mechanical connection to a further component or parts of a component of the ossicular chain, or directly to the inner ear, and including an elongated connecting element that connects the two fastening elements in a sound-conducting manner.

A passive ossicle prosthesis of this type is made known, e.g., in DE 20 2007 012 217 U1.

Ossicle prostheses of this type are used to improve sound transmission in patients having different pathologies. They are used to conduct sound from the tympanic membrane to the inner ear in cases in which the ossicles of the human middle ear are missing or damaged, either entirely or partially. The ossicle prosthesis has two ends; depending on the specific circumstances, one end of the ossicle prosthesis is fastened to the tympanic membrane, e.g., using a top plate, and the other end of the ossicle prosthesis is fastened, e.g., to the stapes of the human ossicular chain, or it is inserted directly into the inner ear.

Three types of ossicle prostheses used particularly frequently are stapes prostheses, partial prostheses, and total prostheses. Stapes prostheses are fixed to the incus or the manubrium of malleus, and extend via a piston into the inner ear. Partial prostheses typically bear via a top plate against the tympanic membrane and establish a connection to the head of the stapes. Total prostheses connect the tympanic membrane to the base of the stapes.

The maximum length of implantable, passive ossicle prostheses of this type is on the order of only a few millimeters, which makes practical handling of the prostheses difficult. For surgical implantation in the human middle ear, surgeons typically use a microscope as well as suitable special instruments such as pincers, tweezers, fine needles, microsuction devices, and the like.

U.S. Pat. No. 6,892,466 B2 describes a special applicator designed to insert mock-ups of prostheses into the middle ear in order to determine the actual size of an individual ossicle prosthesis required for a particular patient. Since the prosthesis mock-ups described therein should match the ossicle prostheses to be used as closely as possible in terms of shape and size, an applicator of this type would also be suitable for use, of course, to insert the actual prostheses.

However, the disadvantage of the use of these known applicators is that they must be thoroughly disinfected and sterilized before the surgery takes place, as is the case for every other surgical instrument. Furthermore, these applicators are typically not specially matched in terms of shape and size to the ossicle prosthesis current being used, and so several different applicators must be made available in advance if the aim is to ensure that a certain prosthesis may be selected from the rather large assortment that is available. Otherwise the surgeon must quickly decide, during surgery, which of the available applicators he wants to use to handle the prosthesis selected on an ad hoc basis to be inserted into the middle ear of the patient; this approach often results in a less-than-optimal selection of the tool and, therefore, to a further complication of the implantation operation which is not trivial to start with.

This may result in a further, even more serious problem: Since the dimensions involved are so small, surgery in the middle ear must take place under the microscope. During the first stage, the microscope is directed by the operating surgeon onto the surgical site, i.e., the auditory meatus or the middle ear. When the point is reached during surgery at which the ossicle prosthesis should be inserted, the microscope usually remains sharply focused on the region of the middle ear observed most recently, of course, while the prosthesis is removed from its sterile packaging in which it is stored and shipped. For this purpose, most operating surgeons use an instrument which has typically not been optimized for this application, nor do they use the microscope which has been focused on the surgical site; instead, they reach, in particular, for the prosthesis, without magnification, and "by feel and using the naked eye". In so doing, the ossicle prosthesis often becomes damaged or is even destroyed, thereby making it necessary to insert another implant in the region of the auditory meatus or the middle ear.

However, reaching for and handling a device as small as an ossicle prosthesis and, in particular, placing it and orienting it in exactly the proper place in the middle ear should be carried out using the finest precision possible, and, mainly, in a routine, standardized manner.

SUMMARY OF THE INVENTION

The object of the present invention, therefore, is to improve a passive ossicle prosthesis of the type in question and described initially using the simplest technical means possible such that it may be removed from the typical sterile packaging by the surgeon in a standardized manner and immediately inserted directly into the auditory meatus of the patient—without elaborate pretreatment or the subsequent use of additional instruments—, and implanted into the middle ear, while ensuring that handling during the implantation operation is as optimal as possible and tailored to the geometry of the particular prosthesis that was selected, and, in particular, nearly ruling out the possibility of damage occurring solely via the gripping and transfer of the prosthesis.

According to the present invention, this object is attained in a manner that is as surprisingly simple as it is effective by providing an elongated applicator for use to transfer the ossicle prosthesis from a sterile packaging to the surgical site and inserting it into the middle ear or the auditory meatus, the applicator including a free end extending away from the ossicular prosthesis and used for handling purposes, and including an engagement part which is initially fastened to the ossicle prosthesis in a non-positive or form-fit manner, or via a detachable or shearable material bridge, and, once the ossicle prosthesis is inserted in the middle ear or the auditory meatus, may be detached from the ossicle prosthesis and removed, together with the applicator, from the middle ear or the auditory meatus.

This makes it possible to provide, in a simple, low-cost manner, a unit composed of an ossicle prosthesis and an individual transfer means optimally tailored to its geometry, which may be removed from the sterile packaging in a manner such that it is ready for surgical use. Once the prosthesis has been implanted, the applicator may be easily removed from the middle ear and discarded, thereby greatly simplifying the practical handling, by the surgeon, of the ossicle prosthesis according to the present invention. The entire procedure is standardized, and, except for the surgical microscope, no further instruments are necessary, and, in particular, there is no need to perform sterile pretreatment of the same.

Embodiments of the present invention are particularly preferably in which the applicator is fastened to a first fastening element of the ossicle prosthesis. This design is particularly favorable for ergonomic reasons because the exact placement of the first fastening element in the middle ear is a decisive factor in defining the final placement of the prosthesis in the implanted state. In addition, the first fastening element will typically be the part of the prosthesis located closest to the outer ear, which is why the applicator may be removed from the middle ear most easily from this point, once implantation is complete.

In a first class of embodiments of the present invention, the applicator and its engagement part are fastened to the ossicle prosthesis via a detachable or shearable material bridge having an intended breaking point at which the material of the applicator has a tapered cross section. This geometry may be manufactured in a low-cost manner using relatively simple production engineering. However, after the engagement part is broken off or sheared off, a sharply pointed piece of the material bridge often remains on the ossicle prosthesis. This small tip must be initially located at an uncritical point of the ossicle prosthesis, where there is no subsequent risk of injury or damage occurring to the surroundings due to the remaining bridge piece.

An alternative class of embodiments in which this problem basically never occurs is characterized by the fact that the engagement part of the applicator encloses, in a non-positive and/or form-fit manner, a docking part which is fixedly connected to the ossicle prosthesis. Of course, production is more slightly elaborate in this case than it is to manufacture a simple material bridge. However, this results in many more possibilities for the individual placement and design of the docking region.

Developments of this class of embodiments that are particularly simple to manufacture and handle are those in which the docking part includes a thickened region which is spherical, in particular, in the region in which it is enclosed by the engagement part of the applicator.

Preferably, the engagement part is designed as a clamp or a clip in order to establish a reversible, frictional connection between the engagement part and the docking part.

Variants of the present invention are very particularly preferred in which the applicator is composed—at least in the region of the engagement part—of a material having a memory effect, in particular of Nitinol. Although the use of materials of this type is known per se in the field of ossicle prostheses, it proves particularly effective in conjunction with the present invention in particular. In this manner, once the ossicle prosthesis has been finally placed in the middle ear, heat may simply be applied in order to thermally activate the engagement part, thereby modifying its shape in a specific manner and without mechanical intervention such that the frictional connection between the engagement part and the docking part is released. The applicator may then be easily removed from the middle ear.

In a further class of embodiments of the ossicle prosthesis according to the present invention, which also avoids the problem of pointed or sharp-edged pieces of the bridge possibly remaining, the engagement part of the applicator is enclosed, in a non-positive and/or form-fit manner, by a receiving part which is fixedly connected to the ossicle prosthesis.

Developments that are particularly simple in terms of production engineering and that may be manufactured at low cost are characterized by the fact that the receiving part is designed as a sleeve that is open in the direction toward the engagement part of the applicator.

Variants of these developments are particularly preferable in which the receiving part includes a cylindrical or conical bore in which a correspondingly shaped, conical end section of the engagement part may engage.

Other variants include a V-shaped gap that is open in the direction toward the engagement part of the applicator, as the receiving part, in which a wedge-shaped end section of the engagement part may engage.

In another group of developments of the above-described embodiment, the engagement part has a thickened region which is enclosed by the receiving part in the manner of a clamp. The receiving part is composed, at least in the region of the engagement part, of a material having memory effect, in particular of Nitinol. In this variant of the present invention as well, the thermal activation described above in conjunction with other embodiments may take place by inducing a predetermined change in shape by applying heat to the receiving part and thereby eliminating the non-positive or form-fit connection between the engagement part and the docking part.

As an alternative, in further simple variants that are particularly geometrically compact, the first fastening element may have the shape of a clamp or clip, and, on its inner side, it may include a region designed as a receiving part for receiving the engagement part.

The ossicle prosthesis according to the present invention may have very different mechanical characteristics depending on the desired field of application and the particular defect to be eliminated or at least ameliorated in terms of its effect on the patient via the use of the ossicle prosthesis according to the present invention: For example, a fastening element acting as a clamping part may be designed approximately as a clamp, a cuff, a sleeve, a clip, a buckle, a clamping ring, or a belt. The fundamental idea behind the present invention may therefore be applied in an approximately universal manner in the field of middle ear prosthetics.

In many embodiments, the prosthesis may be attached, e.g., to the limb of incus or to the stapes, or it may be inserted directly into the inner ear. In this context, an embodiment is advantageous in which the ossicle prosthesis is located at the end of the hammer (=umbo) or directly adjacent thereto, thereby resulting in the greatest leverage for the mechanical transmission of sound via motions that occur in the artificial or natural ossicular chain.

One class of embodiments of the inventive ossicle prosthesis is characterized by the fact that the second fastening element is designed as a plate, a sleeve, a loop, as a closed bell, as a bell having one or two slots, or as a clip for mechanical connection to a further element of the ossicular chain.

In developments of these embodiments, the prosthesis is fastened to the tympanic membrane at one end via a first fastening element designed as a top plate, and to the incus or stapes at the other end via the second fastening element.

Alternative embodiments may provide that the ossicle prosthesis is coupled via its end to which the second fastening element is attached via perforation of the stapes (stapedectomy or stapedotomy), and/or by opening up the human cochlea (=cochleotomy), to which the top plate is attached at the opposite end, directly to the inner ear, using a plunger, in particular.

After the prosthesis has been surgically implanted in the middle ear and the tympanic membrane has been closed, the recovery phase begins. Scars form during this period, and they produce unforeseeable forces which can cause the prosthesis to move out of its localized position. For this reason, it is very helpful for the prosthesis to have a certain amount of post-surgical mobility, so that the top plate may automatically adapt, post-operatively, to the position of the tympanic membrane. Since, in addition, the unique anatomical features of the ear, such as the position, shape and size of the stapes, incus, hammer and tympanic membrane vary, it is very advantageous when ossicle prostheses are not designed to be completely rigid, but rather to have a certain amount of flexibility or variability.

In the case of the ossicle prosthesis according to the present invention, the connecting element between the two fastening elements is typically designed as an elongated shank, as is well known from the related art. To attain the increased flexibility and variability of the prosthesis described above, it is possible according to a particularly preferred embodiment of the present invention, and as described extensively, e.g., in EP 1 181 907 B1, for at least one ball joint to be provided in the elongated shank. In terms of particularly high post-operative mobility of the prosthesis, developments are particularly advantageous in which the elongated shank includes a large number of further rotary elements which abut each other, preferably in the form of a ball joint chain.

In addition to the post-operative shifting of position, a further problem results once ossicle prostheses have been implanted: The middle ear of the human body may be described as a "semi-open region". Any implantation material inserted in the body within the scope of reconstruction of the middle ear and its structures thereby undergoes a particular stress that predominates in a contaminated and infected environment, and which typically attacks the material. Since the objective of implanting an ossicle prosthesis must always be to enable the implant to remain in the patient's middle ear for as long as possible without complications occurring, a sustained attack on the material may result in damage to the prosthesis and/or in a local infection. Neither of these consequences is tolerable. To permanently prevent damage from occurring to the implantation material or the surrounding tissue, it is provided in a further particularly preferred embodiment of the present invention that the surface of the ossicle prosthesis is coated entirely or at least in sections with a biologically active coating, in particular a growth-inhibiting and/or growth-promoting and/or antibacterial coating.

A first fastening element designed as a tympanic membrane top plate should always include a growth-promoting coating, but a second fastening element that extends directly into the inner ear, e.g., in the form of a plunger, should always include a growth-inhibiting coating.

The ossicle prosthesis, according to the present invention, or parts thereof may be made of titanium and/or gold and/or tantalum and/or steel, and/or an alloy of these metals. It is known that titanium, in particular, in addition to being stiff and having excellent sound-conducting properties, also exhibits excellent biocompatibility with the human ear.

In terms of the post-operative position adjustment described above, embodiments of the present invention are advantageous in which the ossicle prosthesis or parts thereof—in particular one of the fastening elements—is/are made of a material having the above-described memory effect or superelastic properties, Nitinol in particular, as is known, e.g., from WO 02/069850 A1 or U.S. Pat. No. 6,554,861 B2.

As an alternative or in addition thereto, in further embodiments, parts of the ossicle prosthesis according to the present invention may be made of a ceramic material.

Embodiments of the present invention are also possible, however, in which the entire prosthesis or parts thereof are made of biocompatible plastics, particularly silicone, polytetrafluorethylene (PTFE), or fibrous composite materials. By using these materials, is it possible to prevent post-operative rejection reactions from occurring in most cases.

According to a particularly preferred embodiment of the ossicle prosthesis according to the present invention, the mass distribution of the individual parts of the prosthesis is calculated depending on a desired, specifiable frequency response of sound conduction in the middle ear. This allows the sound propagation properties to be tuned to a certain extent using a custom-made ossicle prosthesis without a great deal of additional technical complexity.

In special embodiments, a tuning effect of this type may be attained, e.g., by fastening at least one additional mass to a part of the ossicular chain or the prosthesis depending on a desired, specifiable frequency response of sound conduction in the middle ear. In advantageous developments of these embodiments, the additional mass is fastened to a part of the ossicular chain or the prosthesis using a clip. The additional mass and/or clip may also be coated with a biologically active coating.

Finally, a further embodiment of the present invention is characterized by the fact that the prosthesis is connected to an active vibrating part of a hearing aid which is active and implantable, in particular. This also enables further hearing damage caused by the use of modern electronic devices to be prevented or at least ameliorated in terms of its effect, and a physical connection of the prosthesis to the outside world does not cause a problem—due to the coating described above, when the coating is antibacterial in design—that would result from the increased introduction of bacteria into the region of the middle ear.

Further features and advantages of the present invention result from the detailed description of embodiments of the invention presented below with reference to the figures in the drawing which shows the details that are essential to the present invention. Further features and advantages of the present invention also result from the claims. The individual features may be realized individually, or they may be combined in any possible manner in different variants of the present invention.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENT

The embodiments of ossicle prosthesis 10; 10'; 20; 20'; 30; 40; 50 according to the present invention and depicted schematically in the figures in different levels of detail each includes, at one end, a first fastening element 11; 11'; 21; 21'; 31; 41; 51 which is used to mechanically connect the prosthesis to the tympanic membrane or a component of the ossicular chain, in particular to the limb of incus or the manubrium of malleus. Attached to the other end of ossicle prosthesis 10; 10'; 20; 20'; 30; 40; 50 is a second fastening element 12; 12 for mechanically connecting the prosthesis to a component or parts of a component of the ossicular chain, e.g., via a bell 12 to the base of the stapes, or for direct insertion into the inner ear via a piston 12'. Located between the two is a connecting element 13; 13'; 13'' that connects the two fastening elements 11; 11'; 21; 21'; 31; 41; 51 and 12; 12' in a sound-conducting manner; in all of the embodiments shown, connecting element 13; 13'; 13'' is in the form of an elongated shank.

According to the present invention, an elongated applicator 14; 14'; 24; 24'; 34; 44; 54 is used to transfer the ossicle prosthesis 10; 10'; 20; 20'; 30; 40; 50 from a sterile packaging to the surgical site, and to insert it into the middle ear or the auditory meatus; the applicator includes a free end 15; 15'; 25; 25'; 35; 45; 55 extending away from the ossicular prosthesis and used for handling purposes, and includes an engagement part 16; 16'; 26; 26'; 36; 46; 56 which is initially fastened to the ossicle prosthesis in a non-positive or form-fit manner, or via a detachable or shearable material bridge, and, once the ossicle prosthesis is inserted in the middle ear or the auditory meatus, may be detached from the ossicle prosthesis and removed, together with the applicator, from the middle ear or the auditory meatus.

Figure 1A:
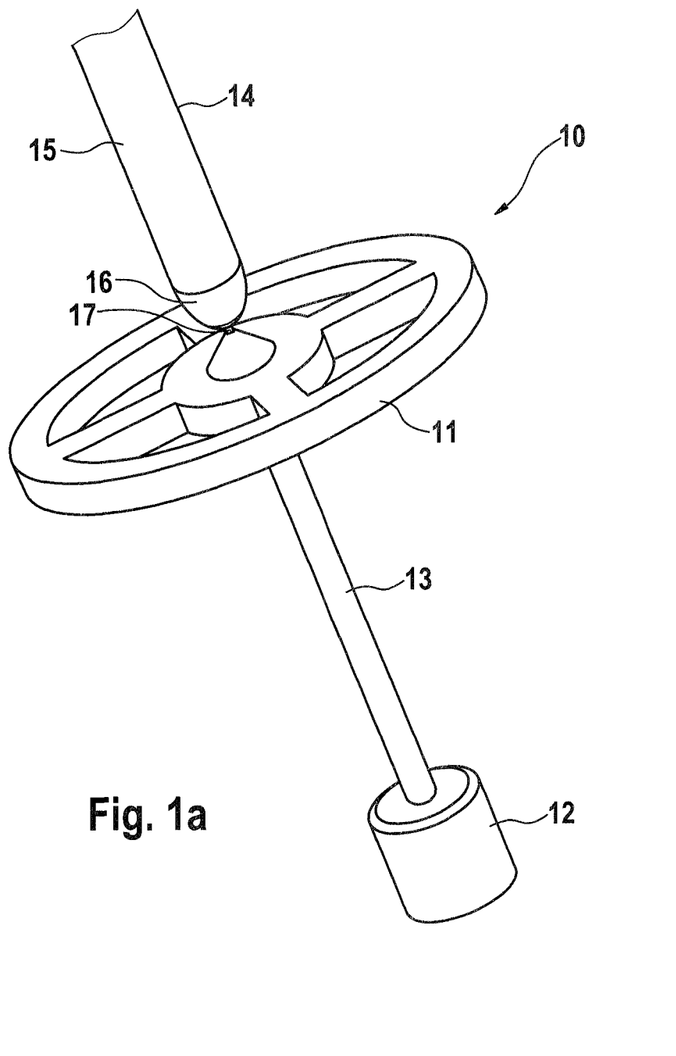
FIG. 1a shows a schematic, spacial depiction of a first embodiment of the ossicle prosthesis according to the present invention, comprising a tympanic membrane top plate as a first fastening element, to which the applicator is attached via a material bridge.
Figure 4A:
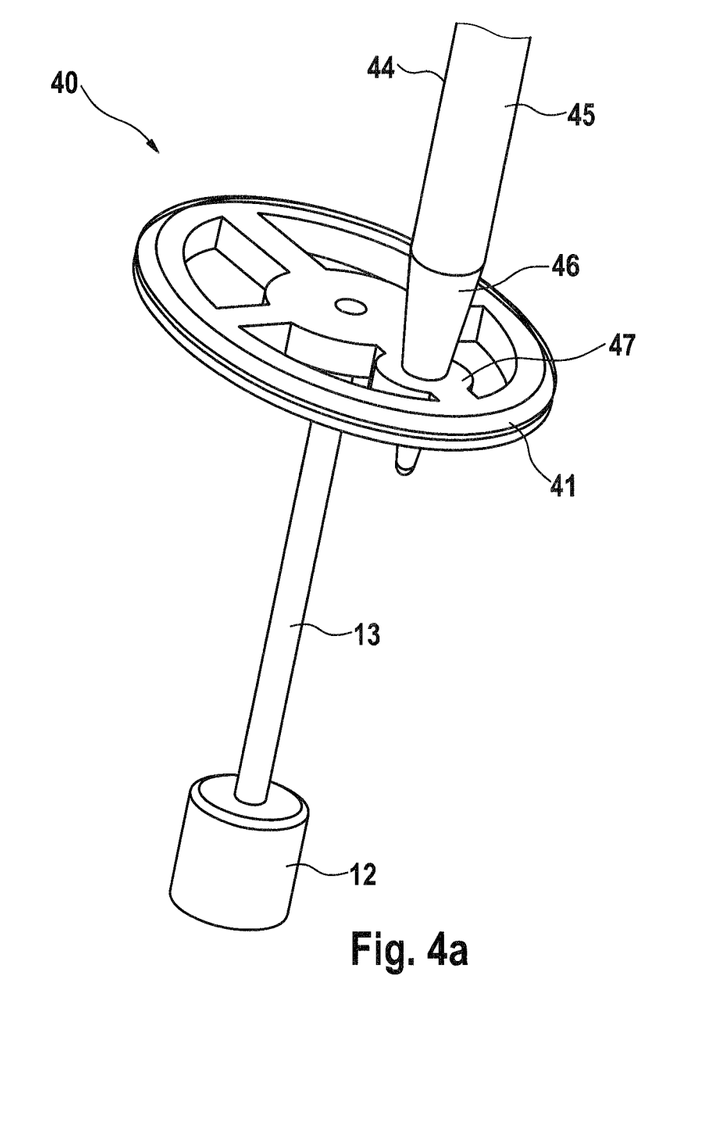
FIG. 4a shows an embodiment comprising a tympanic membrane top plate, as the first fastening element, which includes a sleeve-shaped receiving part having a bore, in which a conical end section of the engagement part of the applicator engages.
Figure 4B:
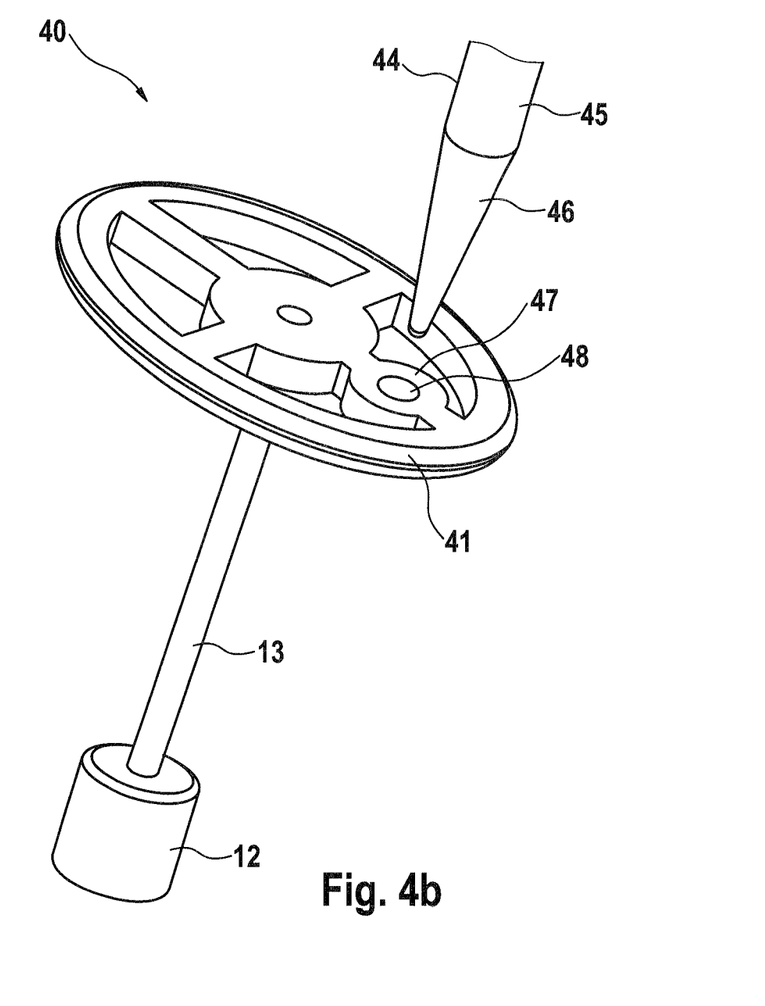
FIG. 4b shows the embodiment in FIG. 4a, in the case of which the applicator has been pulled out of the receiving part of the first fastening element.

In the embodiments shown in FIGS. 1a, 4a, and 4b, first fastening element 11; 41 is in the form of a top plate for placement against the tympanic membrane. In this case, second fastening element 12 is designed in the shape of a bell and is preferably used to fasten ossicle prosthesis 10 to the stapes.

In contrast, in the embodiments shown in FIGS. 1b, 2a, 2b, 3, and 5, first fastening element 11'; 21; 21'; 31; 51 is in the form of a clamp which may be clipped, e.g., to the limb of incus or to another component of the ossicular chain. In these embodiments, second fastening element 12' is designed, at the end opposite the top plate, as a plunger for use to attach ossicle prosthesis 10'; 20; 20'; 30; 50 directly to the inner ear.

In embodiments of the ossicle prosthesis according to the present invention, but which are not shown in the drawings, the second fastening element could instead have a different design, e.g., it could be designed as a plate, a sleeve, a loop, as a partially open hook that is preferably curved in a round shape, a closed bell, as a bell having one or more slits, as a clamp, or as a clip.

Figure 1B:
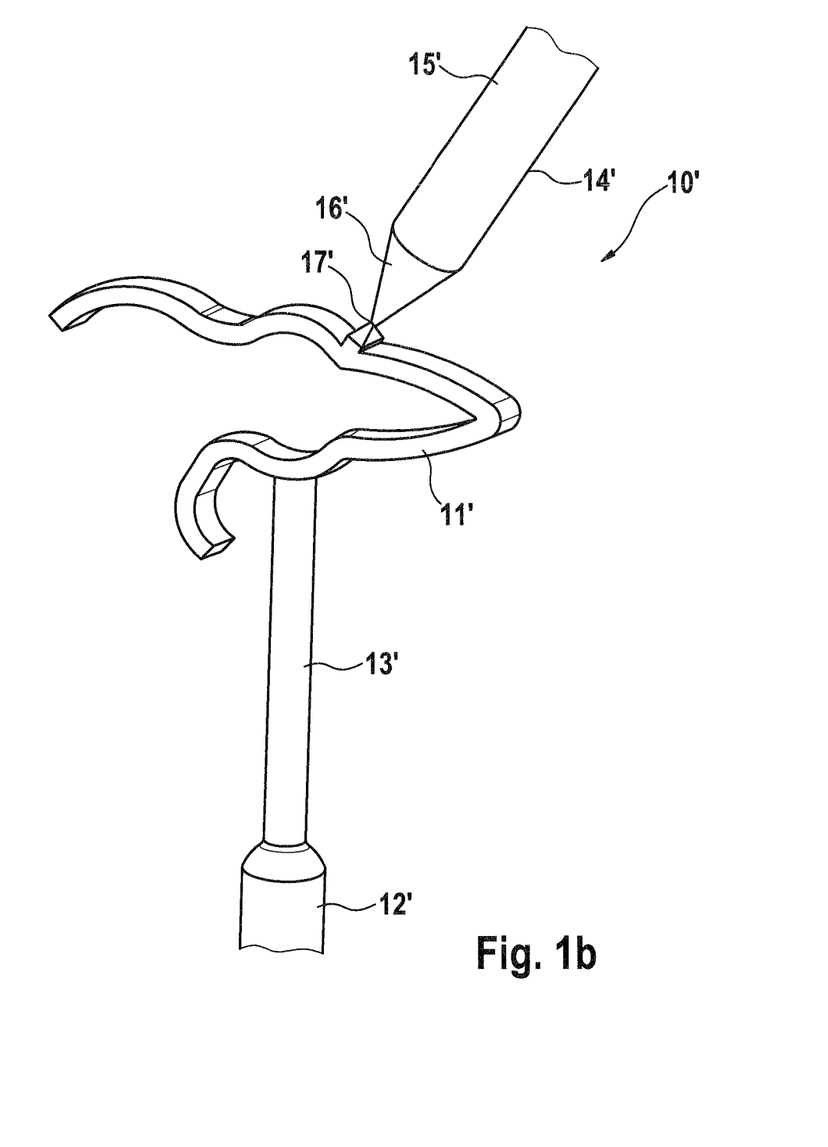
FIG. 1b shows an embodiment comprising a clip as a first fastening element, to which the applicator is attached via a shearable material bridge.

Each of the embodiments shown in FIGS. 1a and 1b includes an applicator 14; 14' which is fastened via its engagement part 16; 16' to ossicle prosthesis 10; 10' via a detachable or shearable material bridge which has an intended breaking point 17; 17' at which the material of applicator 14; 14' has a tapered cross section.

Figure 2A:
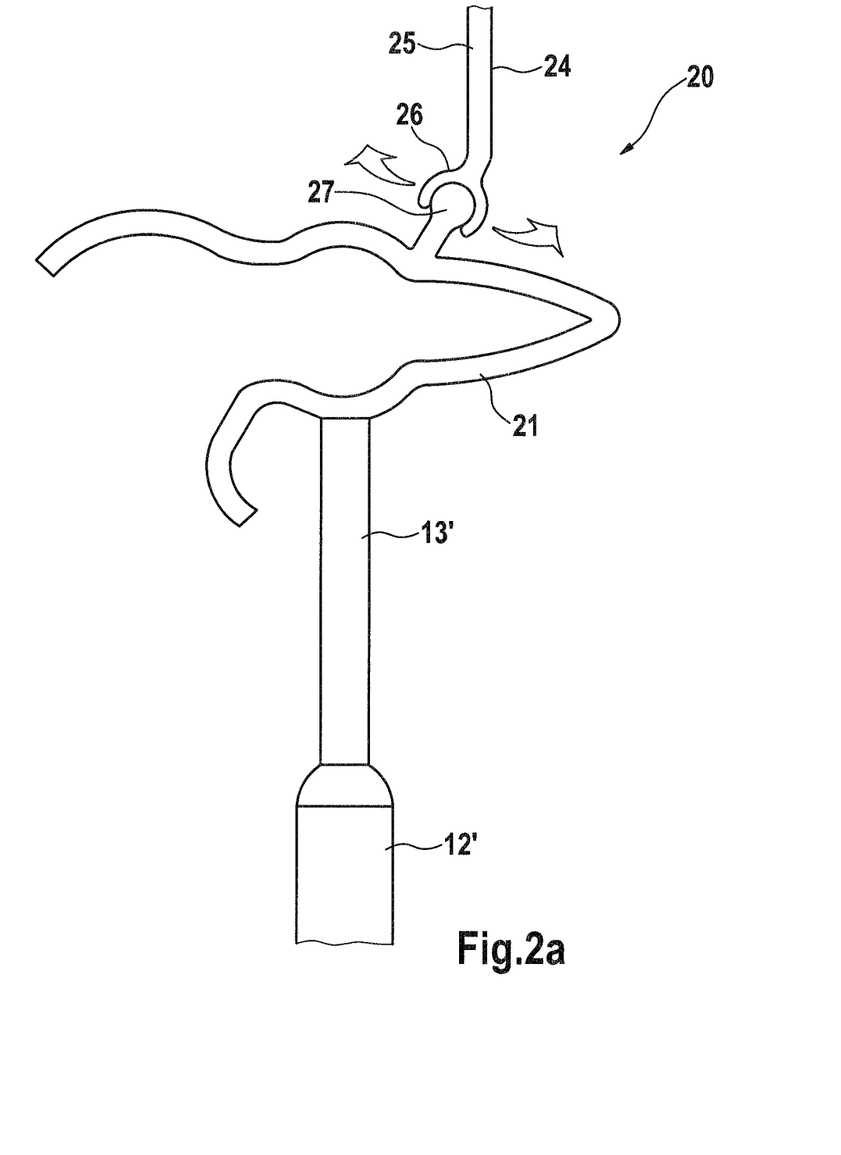
FIG. 2a shows an embodiment comprising a clamp, as a first fastening element, which includes a docking part having a thickened region, and which is enclosed by an engagement part which is initially spread apart in the manner of a clip, and which is composed of a material having a memory effect; the clip-shaped engagement part was subsequently closed around the docking part after application of thermal treatment.
Figure 2B:
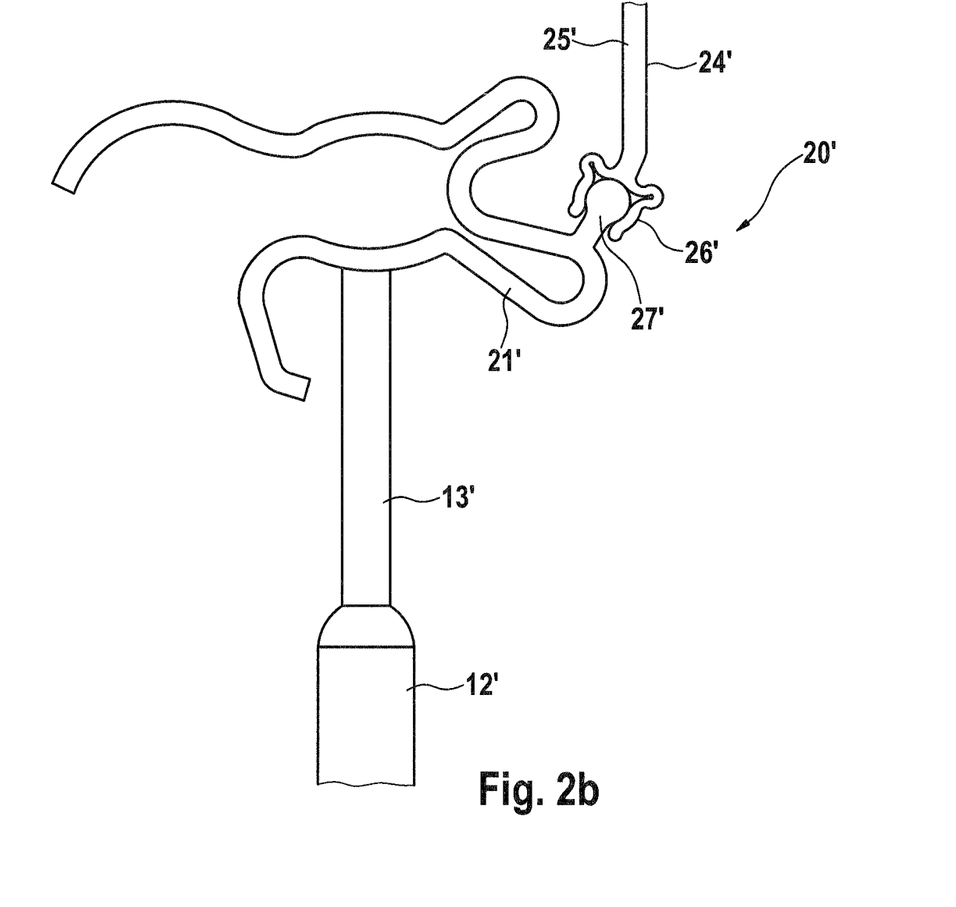
FIG. 2b shows an embodiment comprising a clamp, as the first fastening element, which includes a docking part having a thickened region, and which is enclosed by a clamp-shaped engagement part.

The embodiments shown in FIGS. 2a and 2b are characterized by the fact that engagement part 26; 26' of applicator 24; 24' includes a docking part 27; 27' that is fixedly connected to ossicle prosthesis 20; 20', and which, in these embodiments, includes a spherical thickened region in the region in which it is enclosed by engagement part 26; 26' of applicator 24; 24'; docking part 27; 27' is enclosed by engagement part 26; 26' in a non-positive and/or form-fit manner.

Applicator 24 may be composed, at least in the region of engagement part 26, of a material having memory effect, in particular of Nitinol. The arrows in FIG. 2a indicate that, once ossicle prosthesis 20 has been inserted in its desired position in the ear, clip-shaped engagement part 26 may be spread apart via the simple application of heat in order to pull applicator 24 out of the ear via its free end 25.

Engagement part 26' of applicator 24' shown in FIG. 2b is in the form of a clamp which is clipped onto spherical docking part 27' using mild contact pressure, and which, once ossicle prosthesis 20' has been inserted into the auditory meatus of the patient, or once it has been placed in its final position in the middle ear, may be easily removed from first fastening element 21', in order to then remove applicator 24'.

Figure 3:
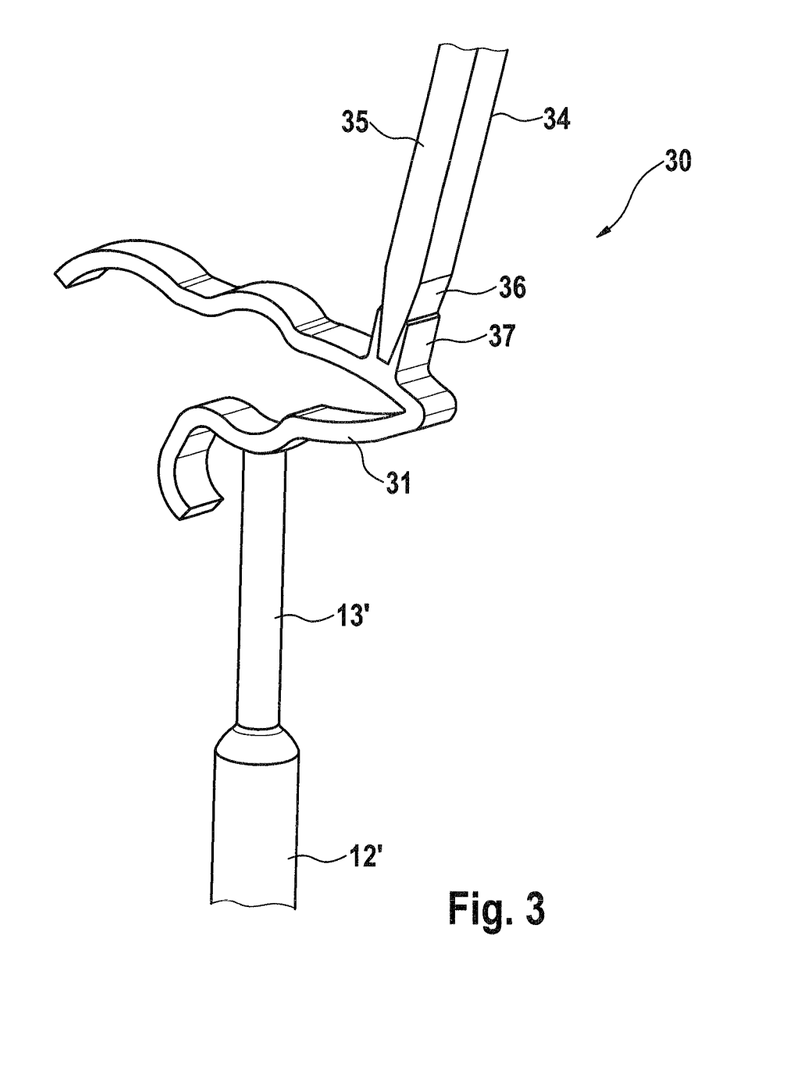
FIG. 3 shows an embodiment comprising a clamp, as the first fastening element, which has a V-shaped gap, as the receiving part, in which a wedge-shaped end section of the engagement part of the applicator engages.
Figure 4C:
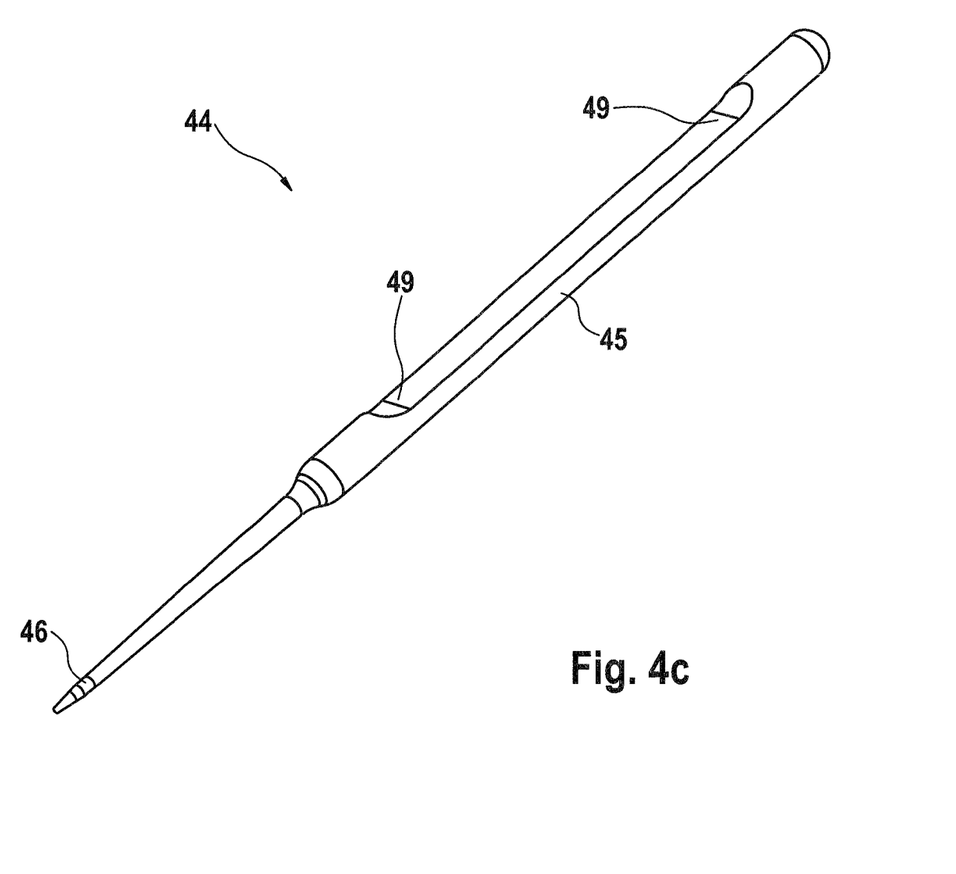
FIG. 4c shows the applicator in FIGS. 4a and 4b in greater detail.
Figure 5:
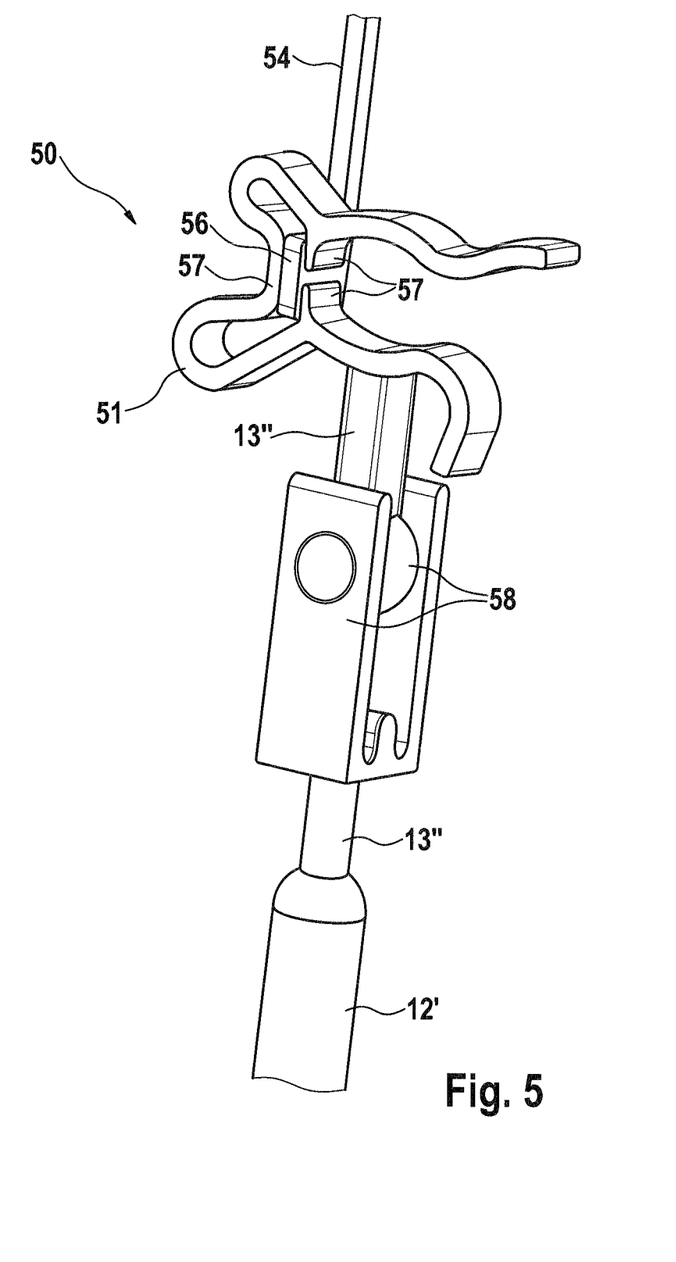
FIG. 5 shows an embodiment comprising a clamp, as the first fastening element, which includes a region on its inner side designed as a receiving part for accommodating the engagement part of the applicator in a form-fit manner.

In the embodiments shown in FIGS. 3 through 5, engagement part 36; 46; 56 of applicator 34; 44; 54 is enclosed, in a non-positive and/or form-fit manner, by a receiving part 37; 47; 57 which is fixedly connected to the prosthesis until ossicle prosthesis 30; 40; 50 has been placed in its final position in the middle ear, or until it has been inserted in the auditory meatus.

Ossicle prosthesis 30 shown in FIG. 3 includes, on its first fastening element 31, a receiving part 37 designed as V-shaped gap which is open in the direction toward engagement part 36 of applicator 34, into which a wedge-shaped end section of engagement part 36 engages in a lightly clamping manner until the prosthesis has been placed or positioned in the ear. It may then be easily removed via free end 35 of applicator 34.

In the embodiment shown in FIGS. 4a through 4c, receiving part 47 is designed as a sleeve which is open in the direction toward engagement part 46 of applicator 44, and which includes a cylindrical or conical bore 48 into which a conical end section of engagement part 46 initially engages in a lightly clamping manner (FIG. 4a), and which may be easily withdrawn at a later point in time by removing applicator 44 (FIG. 4b).

FIG. 4c shows pin-shaped applicator 44 in greater detail, including its pointed engagement part 46 and a free end 45 which includes an ergonomically favorable, unilateral recess 49 for improving the handling of applicator 44.

Finally, in the embodiment depicted in FIG. 5, a ball joint 58 is integrated in connecting element 13" in order to attain a certain level of post-operative flexibility of ossicle prosthesis 50 between its connection points. First fastening element 51 is in the shape of a clamp in this case. On its inner side it includes a region designed as receiving part 57 for receiving engagement part 56, and from which engagement part 56 may be easily removed, after ossicle prosthesis 50 has been positioned in the ear, in order to remove applicator 54.

In embodiments of the ossicle prosthesis, according to the present invention, which are not depicted separately in the drawings, the engagement part of the applicator may include a thickened region which is enclosed by the receiving part of the first fastening element in the manner of a clamp, the receiving part being composed—at least in the region of the engagement part—of a material having a memory effect, in particular of Nitinol. Once the ossicle prosthesis has been placed in the ear, the engagement part may be detached from the receiving part via application of heat, and it may be removed from the applicator.

The mass distribution of the individual parts of ossicle prosthesis 10; 10'; 20; 20'; 30; 40; 50, according to the present invention, may be calculated as a function of a desired, specifiable frequency response of sound conduction in the middle ear such that it is possible to tune the sound propagation properties in an individualized manner. In embodiments that are not depicted in the drawings, at least one additional mass may be fastened to the ossicle prosthesis or to a part of the ossicular chain, using a clip in particular, depending on a desired, specifiable frequency response of sound conduction in the middle ear.

It will be understood that each of the elements described above, or two or more together, may also find a useful application in other types of constructions differing from the types described above.

While the invention has been illustrated and described as embodied in a passive ossicle prosthesis comprising applicator, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention. What is claimed as new and desired to be protected by Letters Patent is set forth in the appended claims.

The invention claimed is:

1. A device for replacement or bridging at least one component of a human ossicular chain, comprising:
an ossicle prosthesis, comprising a first fastening element provided on a first end for mechanical connection to a tympanic membrane or a component of the ossicular chain; a second fastening element provided on a second end for mechanical connection to a further component or parts of the further component of the ossicular chain or directly to an inner ear; an elongated connecting element that connects said first fastening element to said second fastening element in a sound-conducting manner; the first fastening element having a receiving bore formed therein; and
an elongated applicator fixedly connected to the ossicle prosthesis adapted to transfer the ossicle prosthesis from a sterile packaging to a surgical site; wherein said elongated applicator has a length and width enabling said elongated applicator to be inserted into a middle ear or an auditory meatus, said elongated applicator including a first end and a second end, the first end having a handle portion extending away from the ossicle prosthesis and used for handling purposes, the second end having an engagement part;
wherein said engagement part is disposed within the receiving bore such that the receiving bore clamps the engagement part in a form-fit manner, thereby fixedly connecting the ossicle prosthesis to the elongated applicator such that the ossicle prosthesis and elongated applicator form one unit that is removable form the sterile packaging in a manner such that both the ossicle prosthesis and elongated applicator are ready for surgical use;
wherein once the ossicle prosthesis has been inserted into the middle ear or auditory meatus, the engagement part is detachable from the receiving bore and removable together with said elongated applicator from the middle ear or auditory meatus, leaving the ossicle prosthesis in place.

2. The device ossicle prosthesis as defined in claim 1, wherein said receiving bore is formed as a sleeve which is open in a direction towards said engagement part of said applicator, and which includes a cylindrical or conical bore into which a conical end section of said engagement part is engageable.

3. The device as defined in claim 1, wherein said first fastening element is formed as a tympanic membrane top plate for placement against a tympanic membrane, and wherein said elongated applicator is fastened, when the ossicle prosthesis is in an implanted state, to a first side of said tympanic membrane top plate facing the tympanic membrane.

4. The device as defined in claim 3, wherein said elongated applicator is fastened to a center of the tympanic membrane top plate on said first side of said tympanic membrane top plate, said first side of said tympanic membrane top plate being opposite a second side of said tympanic membrane to plate where elongated connecting element contacts said tympanic membrane top plate.

* * * * *